United States Patent [19]
Mori

[11] Patent Number: 4,911,511
[45] Date of Patent: Mar. 27, 1990

[54] LIGHT RAY RADIATION STAND

[76] Inventor: Kei Mori, 3-16-3-501, Kaminoge, Setagaya-ku, Tokyo, Japan

[21] Appl. No.: 200,485

[22] Filed: May 31, 1988

[30] Foreign Application Priority Data

Sep. 21, 1987 [JP] Japan .................................. 62-238338

[51] Int. Cl.⁴ ............................ G02B 6/00; G02B 6/14
[52] U.S. Cl. .................................................. 350/96.10
[58] Field of Search ................ 350/96.10, 96.15, 96.20

[56] References Cited

U.S. PATENT DOCUMENTS

| | | | |
|---|---|---|---|
| 3,723,722 | 3/1973 | Van Iderstine | 350/96.10 |
| 4,297,000 | 10/1981 | Fries | 350/96.10 |
| 4,307,936 | 12/1981 | Ochiai | 350/96.10 |
| 4,626,064 | 12/1986 | Futagawa | 350/96.10 |

Primary Examiner—William L. Sikes
Assistant Examiner—Robert E. Wise
Attorney, Agent, or Firm—Jordan and Hamburg

[57] ABSTRACT

A light ray radiation stand capable of radiating light rays transmitted through an optical conductor cable in an optical desired direction comprises a foundation, a deformable flexible conduit vertically installed on the foundation, and an optical conductor cable. The optical conductor cable is inserted into the conduit and has one end terminating at the tip end portion of the conduit and another end terminating at the circumferential portion of the foundation through the interior of the foundation. The optical conductor cable is capable of being connected with an optical conductor cable at the side of the foundation. The stand is constructed in such a way that light rays are emitted therefrom at the tip end of the conduit.

8 Claims, 4 Drawing Sheets ready# LIGHT RAY RADIATION STAND

BACKGROUND OF THE INVENTION

The present invention relates to a light ray radiation stand, in particular, a light ray radiation stand capable of radiating the light rays transmitted through an optical conductor cable in an optional desired direction.

In recent years a large number of persons suffer from incurable diseases such as arthritis, neuralgia and rheumatism or pain from injuries, bone fractures, and ill-defined diseases. Furthermore, persons cannot avoid growing old and having ones skin showing aging which happens progressively from a comparatively young age. On the other hand, the present applicant has previously proposed to focus the sun's rays or artificial light rays by using lenses or the like, to guide the same into an optical conductor cable and to transmit those same rays onto an optional desired place through the optical conductor cable. Those light rays, transmitted in such a way, are employed for use in illumination or for other like purposes as for example to cultivate plants, chlorella and the like. In the process thereof, it has been found that visible light rays not containing therein ultraviolet rays, infrared rays, etc. promote a living body reaction and thereby promote the health of a person or prevent a person's skin from showing aging. Furthermore, those visible light rays cause noticeable, beneficial effects of recovering from arthritis, neuralgia, bed-sores, rheumatism, burns, skin diseases, injuries, bone fractures, and the like, and of stopping pain from those diseases. Such beneficial effects have been already witnessed by the present applicant. And further, on the basis of the present applicant's discovery, as mentioned above, the applicant has proposed a light ray radiation device for use in medical treatment capable of performing various kinds of medical treatments or beauty treatments and for promoting the health of persons by radiating the light rays corresponding to the visible light ray components of the sun's rays not containing therein harmful components such as ultraviolet rays or infrared rays.

A light ray radiation device for use in medical treatment as previously proposed by the present applicant has an optical conductor cable and a hood member. At the end portion of the optical conductor cable, the sun's rays or artificial light rays are guided thereinto and guided therethrough. The light rays, (i.e. the white-colored light rays) corresponding to the visible light ray components of the sun's rays, are transmitted through the optical conductor cable as previously proposed by the present applicant in various ways. The hood member is installed at the light-emitting end portion of the optical conductor cable. At the time of administering a medical treatment, a patient is laid on the chair and the light rays consisting of the visible light ray components only are transmitted through the optical conductor cable in the manner mentioned before and radiated onto the diseased part of the patient. The light rays to be radiated onto the diseased part of the patient are the ones corresponding to the visible light ray components of the sun's rays and do not contain therein either harmful ultraviolet rays nor harmful infrared rays. Consequently it is possible to administer medical treatment without harming the person. However, the above-mentioned light ray radiation device, for use in medical treatment, is large and the cost is prohibitive for the average person or family. Furthermore, the device needs much space. Those are the objections to be resolved.

SUMMARY OF THE INVENTION

It is an object of the present invention to provide a light ray radiation stand capable of radiating the light rays transmitted through an optical conductor cable in an optional desired direction.

It is another object of the present invention to provide a light ray radiation stand which can be preferably employed in a family setting.

It is another object of the present invention to provide a light ray radiation stand which is low-cost; which is capable of being easily transported around; which doesn't need much space, and which can radiate the light rays in an optional desired direction and thereby can be used very readily.

DESCRIPTION OF THE PREFERRED EMBODIMENTS

Figure 1:
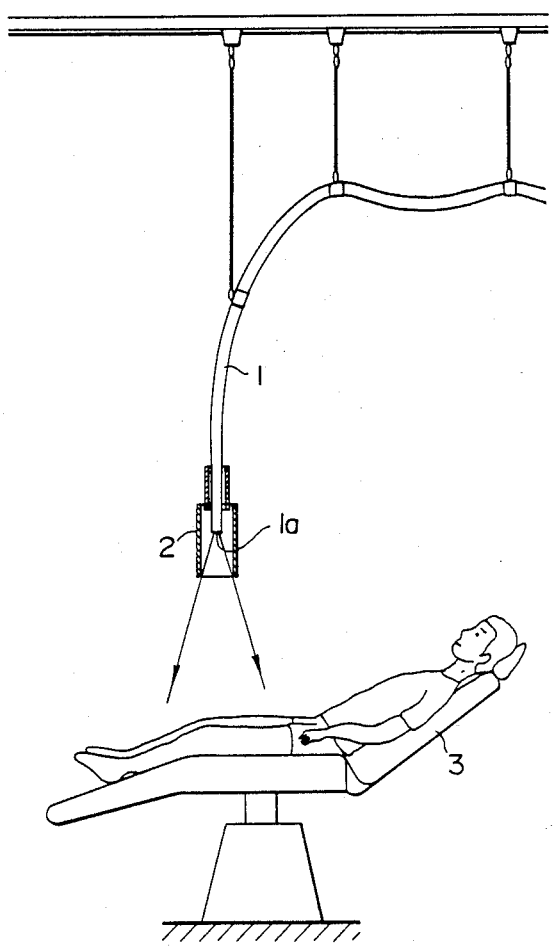
FIG. 1 is a view for explaining an embodiment of a light ray radiation device for use in medical treatment as previously proposed by the present applicant.

FIG. 1 shows an embodiment of a light ray radiation device for use in medical treatment as previously proposed by the present applicant. In FIG. 1, 1 is an optical conductor cable. At the end portion thereof not shown in FIG. 1, the sun's rays or artificial light rays collected by means of a sun ray-collecting device not sown in FIG. 1 are guided thereinto and guided therethrough. The light rays, (i.e. the white-colored light rays) corresponding to the visible light ray components of the sun's rays, are transmitted through the optical conductor cable 1 as previously proposed by the present applicant in various ways. In FIG. 1, 2 is a hood member installed at the light-emitting end portion 1a of the optical conductor cable 1, and 3 is a chair for use in medical treatment. At the time of administering a medical treatment, a patient is laid on the chair 3 and the light rays consisting of the visible light ray components only are transmitted through the optical conductor cable 1 in the manner mentioned before and radiated onto the diseased part of the patient. The light rays to be radiated onto the diseased part of the patient are the ones corresponding to the visible light ray components of the sun's rays and do not contain therein either harmful ultraviolet rays nor harmful infrared rays. Consequently it is possible to administer medical treatment without harming the person. However, the above-mentioned light ray radiation device, for use in medical treatment, is large and the cost is prohibitive for the average person or family. Furthermore, the device needs much space. Those are the objections to be resolved.

Figure 2:
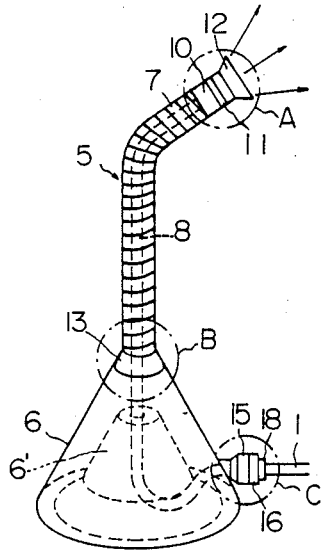
FIG. 2 is an entire perspective view for explaining an embodiment of a light ray radiation stand according to the present invention.
Figure 5:
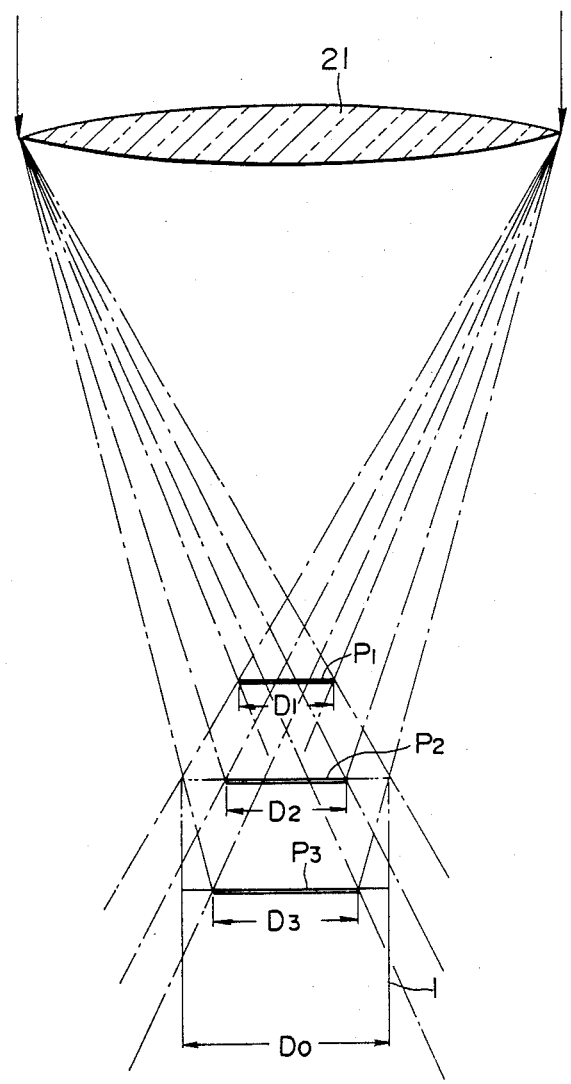
FIG. 5 is a view for explaining an example for guiding the sun's rays into the optical conductor cable.

FIG. 2 is a perspective view for explaining an embodiment of a light ray radiation stand according to the present invention. In FIG. 2, 1 is an optical conductor cable for transmitting therethrough the sun's rays collected by means of a sun ray-collecting device not shown in FIG. 2 and 5 is a light ray radiation stand according to the present invention.

The light ray radiation stand 5 comprises a hollow foundation 6, a deformable flexible conduit 7 installed on the foundation 6, and an optical conductor cable 8 inserted into the conduit 7. The optical conductor cable 8 is constructed in such a way that one end thereof is extended to the tip end portion of the conduit 7 and another end thereof is extended to the hollow portion 6' of the foundation 6 or extended to the circumferential portion of the foundation through the hollow portion of the same and the optical conductor cable 8 is detachably connected with the afore-mentioned optical conductor cable 1 at the outside of the foundation 6. When the optical conductor cable 8 is connected with the optical conductor cable 1, the light rays transmitted through the optical conductor cable 1 are transmitted to the optical conductor cable 8. Next, the light rays are transmitted through the optical conductor cable 8 and emitted from the tip end thereof.

Figure 3A:
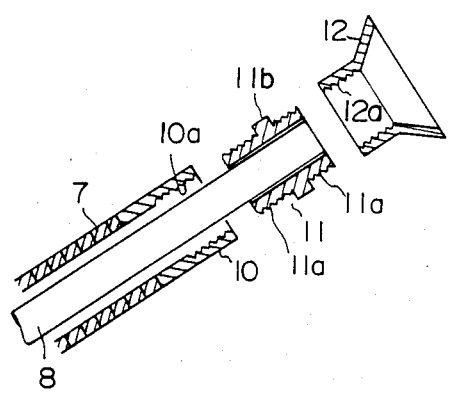
FIG. 3(a) is an enlarged cross-sectional view of the portion A shown in FIG. 2.
Figure 3B:
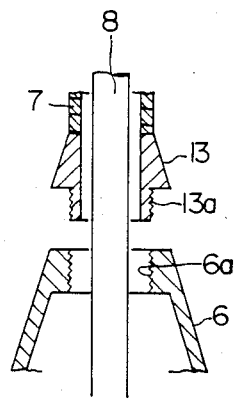
FIG. 3(b) an enlarged cross-sectional view of the portion B shown in FIG. 2.
Figure 3C:
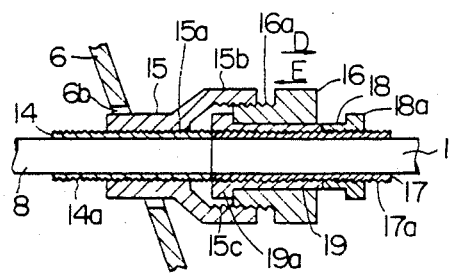
FIG. 3(c) an enlarged cross-sectional view of the portion C shown in FIG. 2.

FIG. 3(a) is an enlarged cross-sectional view of the portion A shown in FIG. 2, FIG. 3(b) an enlarged cross-sectional view of the portion B shown in FIG. 2, and FIG. 3(c) an enlarged cross-sectional view of the portion C shown in FIG. 2. In FIGS. 3(a) through 3(c), reference numerals 7 and 8 represent the conduit and the optical conductor cable both shown in FIG. 2, respectively. The tip end portion of the conduit 7 is jointed by welding, etc. to a nipple 10 having a threaded portion 10a on the internal side thereof, as shown in FIG. 3(a). And further, the tip end portion of the optical conductor cable 8 is bonded by use of adhesive or the like to a terminal metal fixture 11 having a threaded portion 11a on the external circumferential portion thereof. At the time of assembling, the male screw 11a of the terminal metal fixture 11 is screwed into the female screw 10a of the nipple 10.

In the case of the embodiment shown in FIG. 3(a), a flange 11b is formed on the almost central portion of the terminal metal fixture 11. The flange 11b is employed for restricting the amount of screwing the terminal metal fixture. However, it is not always necessary to form such the flange. The reference numeral 12 represents a hood member. The hood member 12 has a female screw 12a to be engaged with the male screw 11a of the afore-mentioned terminal metal fixture 11. When the tip end portion of the conduit is assembled by engaging those screws 10a, 11a and 12a with each other, its state of being assembled turns out to be as shown by the portion A in FIG. 2.

FIG. 3(b) is an enlarged cross-sectional view of the portion B shown in FIG. 2. In FIG. 3(b), the other tip end portion of the afore-mentioned conduit 7 is jointed by welding, etc. to a metal mount 13. A screw 13a is formed on the outer circumference at the tip end portion of the connection metal mount 13. At the time of assembling, the male screw 13a of the metal mount 13 is screwed into the female screw 6a of the foundation 6. The conduit 7 is firmly fixed on a foundation 6 as shown by the portion B in FIG. 2.

FIG. 3(c) is an enlarged cross-sectional view of the portion C shown in FIG. 2. As shown in FIG. 3(c), there is provided a hole 6b for taking out the end portion of the optical conductor cable 8 outside of the foundation 6, at the side portion of the foundation 6. The optical conductor cable 8 is connected with the optical conductor cable 1 at the external side of the foundation 6 as shown by the portion C shown in FIG. 2. Namely, the tip end portion of the optical conductor cable 8 is unitarily jointed by use of adhesive or the like to the inner surface of the portion pipe 14 having a male screw 14a on the outer circumferential portion thereof, and further a screw 15a of a terminal coupling 15 is engaged with the screw 14a of the protection tube 14. The terminal coupling 15 has an enlarged cylindrical portion 15b, the diameter of which is larger than the diameter of the hole 6b. In such a construction, the end portion of the optical conductor cable 8 is prevented from being pulled into the foundation 6.

A female screw 15c is formed on the inner surface of the cylindrical portion 15b. A male screw 16a formed on the connection ring 16 of the optical conductor cable 1 is to be engaged with the female screw 15c. Namely, at the end portion of the optical conductor cable 1, a protection pipe 17 similar to the protection pipe 14 of the optical conductor cable 8 is adhesively connected therewith by use of adhesive or the like. A first connection ring supporting member 18 has a stopper-ring portion 18a at one end portion thereof. In such a construction, the connection ring 16 is prevented from slipping out in a direction D shown in FIG. 3c by use of the stopper ring portion 18a.

In such a manner, after threading the first connection ring 18 to the protection pipe 17, the connection ring 16 is inserted onto the first supporting member 18. Afterward, a second connection ring 19 is threaded to the protection tube 17. The second connection ring supporting member 19 has also a stopper ring portion 19a at one end portion thereof. The movement of the connection ring 16 in a direction of an arrow E is restricted by use of the stopper ring portion 19a. The connection ring 16 can be freely moved rotatably around the supporting portions 18 and 19. And further, the same can be moved in a direction of an arrow D or E. Consequently, when the optical conductor cable 8 is connected with the optical conductor cable 1, the connection ring 16 may be threaded to the terminal coupling 15, and when the optical conductor cable 8 is to be disconnected from the other cable 1, the engagement of both optical conductor cables 1 and 8 may be released.

According to the afore-mentioned present invention, since the conduit 7 can be freely deformed or bent and kept in bent position, that way, the light radiation from the optical conductor cable 8 can be bent in a desired direction. Therefore, the light ray radiation stand of the present invention can be used very easily and doesn't need any special facility. Furthermore, when the stand is not being used, the optical conductor cable 1 is detached from the stand, and it can be put back into an optional desired place not needing much space.

Figure 4:
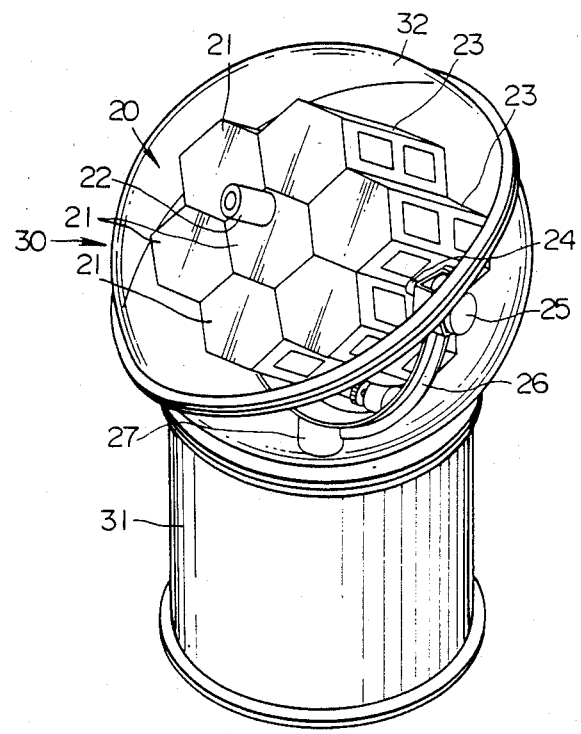
FIG. 4 is a perspective view for explaining an embodiment of a sun ray-collecting device which is used with the present invention.

FIG. 4 is a complete perspective view showing an embodiment of a sun ray-collection device for guiding the sun's rays into the afore-mentioned optical conductor cable 1. In FIG. 4, 31 is a cylindrical foundation and 32 is a transparent dome-shaped head portion. The capsule 30 for use in the sun ray-collecting device is constructed of a fundamental body portion 31 and a head portion 32. As shown in FIG. 4, the sun ray-collecting device 20 is accommodated in the capsule 30 when the device is being used.

The sun ray-collecting device 20 comprises a lens, several lenses or a large number of lenses (as for instance, 7, 19, 61 or 1600 lenses) 21, a sun ray-direction sensor 22 for detecting the direction of the sun, a support frame body 23 for unitarily holding the lens 21 and a sensor 22, a first revolution shaft 24 for rotating the support frame body 23, a first motor 25 for rotating the first revolution shaft 24, a support arm 26 for supporting the lens 21, the sensor 22, the support frame body 23, the first revolution shaft 24, and the first motor 25, a second revolution shaft 27 installed so as to intersect the first revolution shaft 24 perpendicularly thereto, and a second motor, not shown in FIG. 4, for rotating the second revolution shaft 27.

The direction of the sun is detected by means of the sun ray-direction sensor 22 and its detection signal controls the first and second motors so as to always direct the lens 21 toward the sun, and the sun's rays, focused by the lens 21, are guided into the aforementioned optical conductor cable 1 (not shown in FIG. 4), the light-receiving end of which is installed at the focal position of the lens. The guided light rays are transmitted through the optical conductor cable onto an optional desired place.

Concerning the above-mentioned sun ray-collecting device, several types of devices have been proposed heretofore. Those are the devices respectively having a lens or several lenses (2 or 4 lenses) or a larger number of lenses (as for instance, 7, 19, 61 or 196, 1600 lenses) in accordance with the utilization thereof.

FIG. 5 is a detailed view for explaining an example for guiding the light rays corresponding to the visible light ray components of the sun into the optical conductor cable 1. In FIG. 5, 21 is a lens consisting of a Fresnel lens or the like, and 1 is an optical conductor cable as mentioned before for guiding thereinto the sun's rays focused by the lens 21 and for transmitting the guided rays therethrough. In the case of focusing the sun's rays by the use of a lens system, the solar image has a central portion consisting of almost white-colored light rays and a circumferential portion containing therein a large amount of light ray components consisting of the wave lengths corresponding to the focal position of the lens system.

Namely, in the case of focusing the sun's rays by use of the lens system, the position of the lens system and the size of the solar image will vary in accordance with the wave length of the light rays. For instance, the light rays of the color blue having a short wave length make a solar image of diameter $D_1$ at position $P_1$. Furthermore, the light rays of the color green make a solar image of diameter $D_2$ at position $P_2$, and the light rays of the color red make a solar image of diameter $D_3$ at position $P_3$.

Consequently, as shown in FIG. 5, when the light-receiving end-surface of the optical conductor cable 1 is put at position $P_1$, it is possible to collect the rays containing plenty of light rays of the blue color component at the circumferential portion thereof. When the same is put at position $P_2$, it is possible to collect rays containing plenty of light rays of the green color component at the circumferential portion thereof. When the same is put at position $P_3$, it is possible to collect the sun's rays containing plenty of light rays of the red color component at the circumferential portion thereof. In each case, the diameter of the optical conductor cable is determined by the light ray components to be collected. For instance, the diameters thereof are $D_1$, $D_2$ and $D_3$, respectively, depending on the colors of the light rays to be stressed; i.e. the blue, green and red colors. In such a way, the consumed amount of the optical conductor cable can be reduced, and thereby the sun's rays containing therein plenty of light ray components of the desired color can be collected most effectively. And further, as shown in FIG. 5, if the diameter of the light-receiving end-surface of the optical conductor cable 1 is enlarged to $D_0$, it may be possible to collect visible light rays containing therein all of the wave length components.

The visible light rays transmitted through the optical conductor cable 1 in such a way as mentioned above are transmitted to the light ray radiation stand 5 according to the present invention, and the transmitted light rays are guided into the optical conductor cable 8 at the light ray radiation stand 5 and emitted from the tip end portion of the optical conductor cable 8.

As is apparent from the foregoing description, according to the present invention, it may be possible to provide a light ray radiation stand which is low-cost and capable of being freely transported, which doesn't much space, and which can radiate the light rays in an optionally desired direction and thereby used very easily and effectively.

I claim:

1. A light rays radiation stand for receiving solar light rays from an optical conductor and for radiating said solar light rays in a desired direction for effecting medical treatment, comprising a foundation stand having two outer parts spaced from one another, a deformable flexible conduit having one end section and an opposite end section, said one section being connected to one of said outer parts of said foundation stand, said conduit extending generally upwardly from said foundation stand, an optical cable disposed partially in said conduit, said cable having one end and one end portion juxtaposed to said one end, said one end portion extending externally of said one end section of said conduit and passing into said foundation stand from said one foundation stand part to said other foundation stand part such that said one end of said cable is juxtaposed to said other foundation stand part, said conductor having a conductor end, connecting means connecting said one end portion of said cable to said optical conductor such that said one end of said cable abuts said conductor end and light rays are transmitted from said optical conductor to said cable, said connecting means comprising a pipe means disposed about said one end portion of said cable, said pipe means having external threads, and a coupling threaded to said pipe means, said connecting means further comprising mounting means mounted on said conductor, said coupling having fastening means engaging said mounting means, said mounting means comprising a tube means disposed about said conductor, said tube means having external threads, a supporting ring means threaded onto said threads of said tube means, and a connecting ring means slidably mounted on said supporting ring means, said connecting ring means having fastening means fastened to said fastening means of said coupling, said cable having an opposite end juxtaposed to said opposite end section of said conduit, said opposite end of said cable constituting a light-rays emitting end such that light rays transmitted from said optical conductor to said cable are transmitted by said cable to said light-rays emitting end and radiated from said light-rays emitting end in said desired direction for effecting medical treatment.

2. A light rays radiation stand according to claim 1, wherein said supporting ring means comprises two supporting ring elements, each element having an end flange stopper to limit the slidable movement of said connecting ring means on said supporting ring means.

3. A light rays radiation stand according to claim 1, wherein said supporting ring means comprises two supporting ring elements each having a slidable portion on which said connecting ring is slidable, each of said elements having an end flange stopper having an outer diameter greater than the outer diameter of each of said slidable portions.

4. A light rays radiation stand according to claim 1, wherein said coupling has one end which is threaded to said pipe means and another end which has said fastening means which is fastened to said connecting ring means.

5. A light rays radiation stand according to claim 1, wherein said other foundation stand part has an opening, said one end of said coupling being disposed in said opening, said other end of said coupling having an outer diameter greater than the diameter of said opening, said other end of said coupling being located externally of said foundation stand.

6. A light rays radiation stand according to claim 1, further comprising adhesive means adhesively securing said tube means to said optical conductor.

7. A light rays radiation stand for receiving solar light rays from an optical conductor and for radiating said solar light rays in a desired direction for effecting medical treatment, comprising a foundation stand having two other parts spaced from one another, said foundation stand having a frusto-conical configuration having a small top end and a large bottom end with said small top end defining one of said two outer parts, a deformable flexible conduit having one end section and an opposite end section, said one end section being connected to said small top end of said foundation stand, said conduit extending generally upwardly from said foundation stand, an optical cable disposed partially in said conduit, said cable having one end and one end portion juxtaposed to said small top end, said one end portion extending externally of said one end section of said conduit and passing into said foundation stand from said small top end of said foundation stand to said other foundation stand part such that said one end of said cable is juxtaposed to said other foundation stand part, said conductor having a conductor end, connecting means connecting said one end portion of said cable to said optical conductor such that said one end of said cable abuts said conductor end and light rays are transmitted from said optical conductor to said cable, said cable having an opposite end juxtaposed to said opposite end section of said conduit, said opposite end of said cable constituting a light-rays emitting end such that light rays transmitted from said optical conductor to said cable are transmitted by said cable to said light-rays emitting end and radiated from said light-rays emitting end in said desired direction for effecting medical treatment.

8. A light rays radiation device comprising solar ray collecting means for collecting solar light rays, an optical conductor for receiving said solar light rays and for radiating said solar light rays in a desired direction for effecting medical treatment, a foundation stand having two outer parts spaced from one another, a deformable flexible conduit having one end section and an opposite end section, said one end section being connected to one of said outer parts of said foundation stand, said conduit extending generally upwardly from said foundation stand, an optical cable disposed partially in said conduit, said cable having one end and one end portion juxtaposed to said one end, said one end portion extending externally of said one end section of said conduit and passing into said foundation stand from said one foundation stand part to said other foundation stand part such that said one end of said cable is juxtaposed to said other foundation stand part, said conductor having a conductor end, connecting means connecting said one end portion of said cable to said optical conductor such that said one end of said cable abuts said conductor end and light rays are transmitted from said optical conductor to said cable, said cable having an opposite end juxtaposed to said opposite end section of said conduit, said opposite end of said cable constituting a light-rays emitting end such that light rays transmitted from said optical conductor to said cable are transmitted by said cable to said light-rays emitting end and radiated from said light-rays emitting end in said desired direction for effecting medical treatment.

* * * * *